United States Patent
Mori et al.

(10) Patent No.: US 10,301,343 B2
(45) Date of Patent: May 28, 2019

(54) METHOD OF PRODUCING EPIRUBICIN AND NOVEL PRODUCTION INTERMEDIATE THEREOF

(71) Applicant: MEIJI SEIKA PHARMA CO., LTD., Tokyo (JP)

(72) Inventors: Kenichiro Mori, Kanagawa (JP); Takuto Umezu, Kanagawa (JP); Takahisa Maruyama, Iwate (JP); Sojiro Shiokawa, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/562,482

(22) PCT Filed: Mar. 30, 2016

(86) PCT No.: PCT/JP2016/060409
§ 371 (c)(1),
(2) Date: Sep. 28, 2017

(87) PCT Pub. No.: WO2016/159092
PCT Pub. Date: Oct. 6, 2016

(65) Prior Publication Data
US 2018/0094014 A1 Apr. 5, 2018

(30) Foreign Application Priority Data

Mar. 30, 2015 (JP) ................. 2015-067957

(51) Int. Cl.
| | |
|---|---|
| *C07B 63/02* | (2006.01) |
| *C07C 49/423* | (2006.01) |
| *C07H 15/252* | (2006.01) |
| *A61K 31/7008* | (2006.01) |

(52) U.S. Cl.
CPC ....... *C07H 15/252* (2013.01); *A61K 31/7008* (2013.01); *C07B 63/02* (2013.01); *C07C 49/423* (2013.01); *C07B 2200/13* (2013.01); *C07C 2603/44* (2017.05)

(58) Field of Classification Search
None
See application file for complete search history.

(56) References Cited

U.S. PATENT DOCUMENTS

| | | | |
|---|---|---|---|
| 4,112,076 A | 9/1978 | Arcamone et al. | |
| 4,345,068 A | 8/1982 | Suarato et al. | |
| 5,008,380 A * | 4/1991 | Palladino ............. | C07H 15/252 536/18.5 |
| 5,874,550 A | 2/1999 | van der Rijst et al. | |

FOREIGN PATENT DOCUMENTS

| | | |
|---|---|---|
| EP | 0 030 295 | 6/1981 |
| EP | 1 990 405 A1 | 11/2008 |
| EP | 2 192 172 A1 | 6/2010 |
| EP | 2 573 174 A1 | 3/2013 |
| JP | 56-87598 | 7/1981 |
| JP | 7-76515 | 3/1995 |
| JP | 2007-261976 | 10/2007 |
| JP | 2010-525828 | 7/2010 |
| JP | 2013-503826 | 2/2013 |
| WO | 2006/096665 | 9/2006 |
| WO | 2007/076345 | 7/2007 |
| WO | 2008/135195 | 11/2008 |
| WO | 2009/035107 | 3/2009 |
| WO | 2011/029576 | 3/2011 |
| WO | 2011/145211 | 11/2011 |

OTHER PUBLICATIONS

Andorne, HU 206 364 B, Mar. 30, 1992, machine translation.*
Madduri, Nature Biotechnology vol. 16, Jan. 1998, pp. 69-74.*
Pfizer, Prescribing Information for Ellence, Revised Jul. 2011.*
International Search Report dated May 10, 2016 in International (PCT) Application No. PCT/JP2016/060409.
Extended European Search Report dated Nov. 28, 2018 in corresponding European Patent Application No. 16772973.

* cited by examiner

*Primary Examiner* — Layla D Berry
(74) *Attorney, Agent, or Firm* — Wenderoth, Lind & Ponack, L.L.P.

(57) ABSTRACT

According to the present invention, it is possible to efficiently remove 13-dihydroepi-daunorubicin and 4'-epi-feudomycin, which are typical impurities possibly contained in 4'-epi-daunorubicin as a starting material, by using an organic acid salt of 4'-epi-daunorubicin or a hydrate or solvate thereof as a novel production intermediate, thus making it possible to produce high-purity epirubicin.

9 Claims, No Drawings

METHOD OF PRODUCING EPIRUBICIN AND NOVEL PRODUCTION INTERMEDIATE THEREOF

BACKGROUND OF THE INVENTION

Field of the Invention

The present invention relates to a method of producing epirubicin and a salt thereof (for example, a pharmaceutically acceptable salt), as well as a novel production intermediate thereof and a method of producing the intermediate.

Background Art

Epirubicin is an anthracycline antibiotic, and is used for the treatment of acute leukemia, malignant lymphoma, breast cancer, ovarian cancer, stomach cancer, liver cancer, urothelial cancer, and the like. Epirubicin is more excellent in antitumor activity and reduced side effects as compared with daunorubicin and doxorubicin, which are also anthracycline antibiotics, and is a drug which is clinically extremely useful.

As a production method of epirubicin, there is disclosed a method of producing epirubicin through chemical transformation from daunorubicin, a microbial fermentation product, as a starting material. For example, there is disclosed a method of producing epirubicin by dividing daunorubicin into daunomycinone and daunosamine by methanolysis, introducing an acetoxy group at the 14-position of the daunomycinone to convert the daunomycinone to 14-acetoxy daunomycinone, inversing a hydroxyl group at the 4'-position of the amino sugar moiety of the daunosamine to convert the daunosamine to 4'-epi-daunosamine, coupling the 14-acetoxy daunomycinone with the 4'-epi-daunosamine, and converting the resulting compound to epirubicin (Patent Document 1).

The above-mentioned method of producing epirubicin has problems in view of an industrial production method, such as complicatedness and low yield because of requiring multistep synthesis process.

Meanwhile, there is disclosed a method wherein epirubicin is produced in a short step using 4'-epi-daunorubicin or a salt thereof as a starting material (Patent Document 2).

However, this patent document only discloses an example in which 4'-epi-daunorubicin hydrochloride is used as a starting material, and there is neither concrete statement nor illustration about other salts. In addition, there is no statement about purity of epirubicin obtained by this method, and there is no mention about purity of epirubicin hydrochloride obtained by using the illustrated 4'-epi-daunorubicin hydrochloride as a starting material.

Epirubicin has already been disclosed in pharmaceutical standards of various countries, for example, the Japanese Pharmacopoeia, the European Pharmacopoeia, the United States Pharmacopoeia, and the like. Therefore, construction of production technique of high-purity epirubicin, namely, control of impurities in the production is also a problem in view of the production.

Use of a high-purity starting material in order to solve the above-mentioned problems enables reduction in impurities of epirubicin, leading to production of higher-purity epirubicin. Especially, if high-purity 4'-epi-daunorubicin or a salt thereof can be prepared, it will become possible to efficiently produce high-purity epirubicin, thus making it possible to solve the problem in view of an industrial production method.

For example, 4'-epi-daunorubicin is produced by fermentation culture of microorganisms, followed by purification (Patent Document 3 and Non-Patent Document 1). It is known that 4'-epi-daunorubicin produced from a fermentation culture as an origin contains, as typical impurities, 13-dihydroepi-daunorubicin and 4'-epi-feudomycin. There are disclosed a method of converting 4'-epi-daunorubicin into a hydrochloride salt (Patent Document 4, Patent Document 5, and Non-Patent Document 2) and a method of crystallizing 4'-epi-daunorubicin hydrochloride (Patent Document 6).

PRIOR ART DOCUMENTS

Patent Documents

Patent Document 1: U.S. Pat. No. 5,874,550
Patent Document 2: Japanese Unexamined Patent Application Publication No. 2007-261976
Patent Document 3: Japanese Unexamined Patent Application Publication (Translation of PCT Application) No. 2010-525828
Patent Document 4: U.S. Pat. No. 4,112,076
Patent Document 5: U.S. Pat. No. 4,345,068
Patent Document 6: Japanese Unexamined Patent Application Publication (Translation of PCT Application) No. 2013-503826

Non-Patent Documents

Non-Patent Document 1: Nature Biotechnology, 16, 69-74, 1998
Non-Patent Document 2: Carbohydrate Research, 79, 193-204, 1980

SUMMARY OF THE INVENTION

The present inventors carried out purification of 4'-epi-daunorubicin produced by fermentation culture using a purification method known in a person skilled in the art, for example, use of an ion exchange resin and synthetic adsorbent, liquid separation, extraction, and the like so as to prepare high-purity 4'-epi-daunorubicin. However, high-purity 4'-epi-daunorubicin could not be obtained because of low purification effect.

In addition, the present inventors prepared 4'-epi-daunorubicin hydrochloride from 4'-epi-daunorubicin produced by fermentation culture in accordance with a known method, for example, a method of forming 4'-epi-daunorubicin hydrochloride disclosed in Patent Document 4, Patent Document 5, and Non-Patent Document 2. As a result, high-purity 4'-epi-daunorubicin hydrochloride could not be obtained because of low purification effect.

Meanwhile, the present inventors made confirmatory studies on a method of crystallizing of 4'-epi-daunorubicin hydrochloride disclosed in Patent Document 6. As a result, a reduction in 13-dihydroepi-daunorubicin and 4'-epi-feudomycin was observed. However, sufficient effect is not exerted and thus there is a need to repeat crystallization so as to obtain high-purity 4'-epi-daunorubicin hydrochloride. Repetition of crystallization is unsuitable from the viewpoints (yield, operability, and production cost) of an industrial production method.

Thus, an object of the present invention is to provide a novel production intermediate, from which 13-dihydroepi-daunorubicin and 4'-epi-feudomycin, typical impurities possibly contained in 4'-epi-daunorubicin, have been sufficiently removed, an efficient method for producing this intermediate by using 4'-epi-daunorubicin as a starting material, and an efficient method for producing high-purity epirubicin or a salt thereof (for example, a pharmaceutically acceptable salt) by using this intermediate.

As a result of intensive study, the present inventors have found as a novel production intermediate, an organic acid salt of 4'-epi-daunorubicin or a hydrate or solvate thereof, from which 13-dihydroepi-daunorubicin and 4'-epi-feudomycin, typical impurities possibly contained in 4'-epi-daunorubicin, have been sufficiently removed, and a method of efficiently producing this intermediate using 4'-epi-daunorubicin as a starting material, and have also found a method of efficiently producing high-purity epirubicin or a salt thereof (for example, a pharmaceutically acceptable salt) using this intermediate, thus completing the present invention.

Namely, the present invention relates to:

[1] A method of producing an organic acid salt of 4'-epi-daunorubicin or a hydrate or solvate thereof, comprising a step of mixing 4'-epi-daunorubicin of the following formula (1):

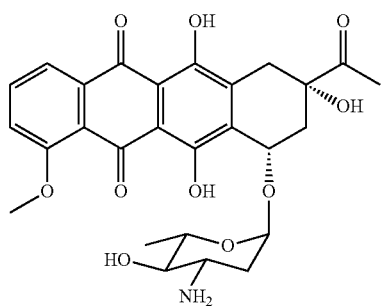

(1)

with an organic acid in a solvent to form an organic acid salt of 4'-epi-daunorubicin of the following formula (2):

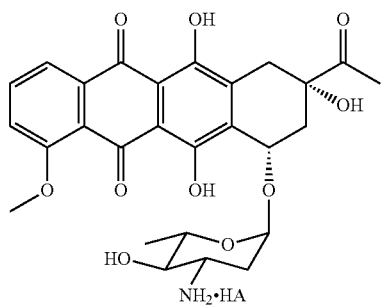

(2)

wherein HA represents an organic acid,
or a hydrate or solvate thereof;

[2] The method according to [1], wherein the step of forming an organic acid salt of 4'-epi-daunorubicin or a hydrate or solvate thereof comprises forming a precipitate of an organic acid salt of 4'-epi-daunorubicin or a hydrate or solvate thereof;

[3] The method according to [1], wherein the step of forming an organic acid salt of 4'-epi-daunorubicin or a hydrate or solvate thereof comprises crystallizing an organic acid salt of 4'-epi-daunorubicin or a hydrate or solvate thereof;

[4] The method according to any one of [1] to [3], wherein the organic acid salt of 4'-epi-daunorubicin is an oxalate;

[5] The method according to any one of [1] to [3], wherein the organic acid salt of 4'-epi-daunorubicin is a benzenesulfonate;

[6] The method according to any one of [1] to [3], wherein the organic acid salt of 4'-epi-daunorubicin is a p-toluenesulfonate;

[7] A method of producing epirubicin or a salt thereof, comprising a step of producing epirubicin of the following formula (3):

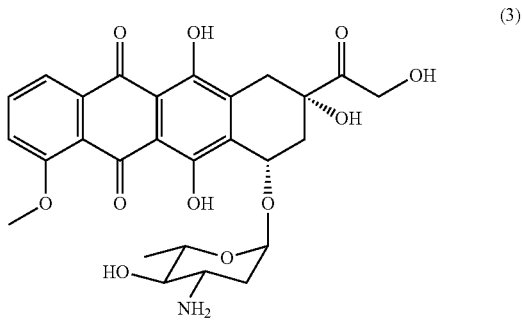 [SMILES: COc1cccc2c1C(=O)c1c(O)c3c(c(O)c1C2=O)C[C@@](O)(C(=O)CO)C[C@@H]3OC1CC(N)C(O)C(C)O1]

(3)

or a salt thereof using, as an intermediate, an organic acid salt of 4'-epi-daunorubicin or a hydrate or solvate thereof, produced by the method according to any one of [1] to [6];

[8] The method according to [7], wherein a final product is epirubicin hydrochloride;

[9] An organic acid salt of 4'-epi-daunorubicin of the following formula (4):

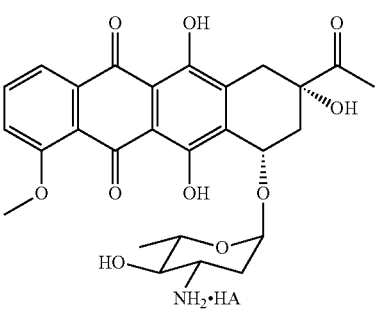

(4)

wherein HA represents oxalic acid, benzenesulfonic acid, or p-toluenesulfonic acid,
or a hydrate or solvate thereof;

[10] An organic acid salt of 4'-epi-daunorubicin or a hydrate or solvate thereof, having a HPLC purity of 90% or more;

[11] The organic acid salt of 4'-epi-daunorubicin or the hydrate or solvate thereof according to [10], wherein the organic acid salt is an oxalate;

[12] The organic acid salt of 4'-epi-daunorubicin or the hydrate or solvate thereof according to [10], wherein the organic acid salt is a benzenesulfonate; and

[13] The organic acid salt of 4'-epi-daunorubicin or the hydrate or solvate thereof according to [10], wherein the organic acid salt is a p-toluenesulfonate.

According to the method of the present invention, it is possible to use 4'-epi-daunorubicin represented by the formula (1) as a starting material to prepare an organic acid salt of 4'-epi-daunorubicin, represented by the formula (2), or a hydrate or solvate thereof as a novel production intermediate, wherein 13-dihydroepi-daunorubicin and 4'-epi-feudomycin, which are typical impurities possibly contained in the 4'-epi-daunorubicin, have been sufficiently removed. It is also possible to use this intermediate to efficiently produce high-purity epirubicin or a salt thereof (for example, a pharmaceutically acceptable salt).

According to the method of the present invention, unlike a method in which 4'-epi-daunorubicin hydrochloride is used, it is possible to effectively remove 13-dihydroepi-daunorubicin and 4'-epi-feudomycin, which are typical impurities possibly contained in the 4'-epi-daunorubicin, by performing a single precipitation in the process of producing an organic acid salt of 4'-epi-daunorubicin or a hydrate or solvate thereof from the 4'-epi-daunorubicin. It is also possible to further remove these impurities by performing a single crystallization of the precipitate of the thus obtained organic acid salt of 4'-epi-daunorubicin or the hydrate or solvate thereof. Therefore, the method of the present invention has an advantage that it is possible to obtain a compound of the formula (2) or a hydrate or solvate thereof, which is used for effectively producing high-purity epirubicin or a salt thereof while keeping a small number of times of purification (short production process).

It is also possible to carry out salification and crystallization of a compound of the formula (2) or a hydrate or solvate thereof using a combination of inexpensive organic acids and general-purpose solvents. The method of the present invention is effective in that a compound of the formula (2) or a hydrate or solvate thereof can be obtained without using complicated operations, and is also a useful method from an industrial point of view, such as production cost.

It is also possible to induce a crystal of the thus obtained high-purity compound of the formula (2) or the hydrate or solvate thereof to high-purity epirubicin or a salt thereof, for example, by the method disclosed in Patent Document 2.

DETAILED DESCRIPTION OF THE INVENTION

The present invention is directed to a method of producing high-purity epirubicin (3) by the following scheme, and an organic acid salt (2) of epirubicin which is a novel production intermediate:

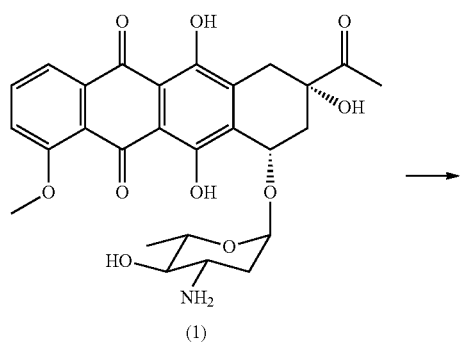

(1)

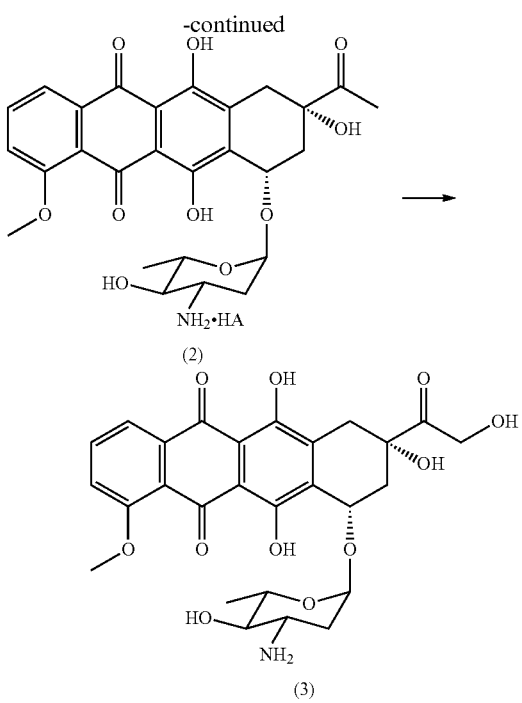

wherein HA represents an organic acid.

It is possible to use, as 4'-epi-daunorubicin represented by the formula (1) used herein, for example, 4'-epi-daunorubicin produced by fermentation culture of microorganisms and subsequent purification of a culture solution (Patent Document 3 and Non-Patent Document 1).

It is also possible to use 4'-epi-daunorubicin produced from daunorubicin, which is produced by fermentation culture, through chemical synthesis transformation.

13-Dihydrodaunorubicin, feudomycin, and the like are known as typical analogs contained in daunorubicin produced by fermentation culture. These analogs undergo inversion of a hydroxyl group at the 4'-position by chemical synthesis transformation, and thus result in 13-dihydroepi-daunorubicin, 4'-epi-feudomycin, and the like, which are contained as impurities in crude 4'-epi-daunorubicin. 13-Dihydroepi-daunorubicin, 4'-epi-feudomycin, and the like are also contained as impurities in crude 4'-epi-daunorubicin produced directly by fermentation culture.

It is also possible to use, as an organic acid used in the present invention, a hydrate of the organic acid. There is no particular limitation on type of the organic acid, and the organic acid is preferably oxalic acid, benzenesulfonic acid, and p-toluenesulfonic acid.

There is no particular limitation on type of an organic acid salt of 4'-epi-daunorubicin represented by the formula (2) of the present invention, or a hydrate or solvate thereof, and the organic acid salt of 4'-epi-daunorubicin or a hydrate or solvate thereof is preferably 4'-epi-daunorubicin oxalate or a hydrate or solvate thereof, 4'-epi-daunorubicin benzenesulfonate or a hydrate or solvate thereof, and 4'-epi-daunorubicin p-toluenesulfonate or a hydrate or solvate thereof.

Specifically, the organic acid salt of 4'-epi-daunorubicin or a hydrate or solvate thereof provided by the present invention can be produced by the following method.

Regarding 4'-epi-daunorubicin oxalate or a hydrate or solvate thereof, 4'-epi-daunorubicin is dissolved in a solvent A, and then oxalic acid or oxalic acid dihydrate dissolved in a solvent B is added to this solution to thereby precipitate 4'-epi-daunorubicin oxalate or a hydrate or solvate thereof. Thereafter, the precipitate is collected by filtration, and then optionally dried under reduced pressure.

As the solvent A, organic solvents used generally by a person skilled in the art can be used. The organic solvent usable as the solvent A is preferably halogenated solvents, specifically dichloromethane, chloroform, or the like, and more preferably dichloromethane. The amount of the solvent A used is not particularly limited as long as it enables dissolution of 4'-epi-daunorubicin, and is preferably in a range of 10 to 400 times the volume of 4'-epi-daunorubicin.

As the solvent B, organic solvents used generally by a person skilled in the art can be used. Examples of the organic solvent usable as the solvent B include methanol, ethanol, 1-propanol, 2-propanol, 1-butanol, 2-butanol, tert-butyl alcohol, acetone, ethyl acetate, tetrahydrofuran, 1,4-dioxane, toluene, acetonitrile, N,N-dimethylformamide, N,N-dimethylacetamide, and the like, and methanol is preferable. The amount of the solvent B used is, for example, in a range of 0.1 to 1 times, and preferably 0.2 to 0.5 times, the volume of the solvent A. The amount of oxalic acid or oxalic acid dihydrate used is, for example, in a range of 1 to 22 equivalents, and preferably 2 to 12 equivalents. The precipitation temperature is a temperature used in a conventional production process and is, for example, in a range of 0 to 30° C., and preferably 15 to 25° C. After precipitation, stirring is optionally performed for a predetermined time. It is acceptable time in manufacturing, for example, 1 hour or more.

It is also possible to prepare 4'-epi-daunorubicin oxalate or a hydrate or solvate thereof by another production method, for example, a method in which 4'-epi-daunorubicin is added to an aqueous solution of oxalic acid or oxalic acid dihydrate to thereby dissolve 4'-epi-daunorubicin, and then an optional solvent is added to this solution to thereby precipitate 4'-epi-daunorubicin oxalate or a hydrate or solvate thereof.

In this case, organic solvents used generally by a person skilled in the art can be used as the optional solvent. Examples of the organic solvent usable as the optional solvent include methanol, ethanol, 1-propanol, 2-propanol, tert-butyl alcohol, acetone, tetrahydrofuran, 1,4-dioxane, acetonitrile, N,N-dimethylformamide, N,N-dimethylacetamide, and the like, and methanol and 2-propanol are preferable. The amount of water used is, for example, in a range of 5 to 50 times, and preferably 10 to 20 times, the volume of 4'-epi-daunorubicin. The amount of the optional solvent used is, for example, in a range of 1 to 10 times, and preferably 1 to 5 times, the volume of water. The amount of oxalic acid or oxalic acid dihydrate used is, for example, in a range of 1 to 10 equivalents, and preferably 1 to 5 equivalents. The precipitation temperature of 4'-epi-daunorubicin oxalate or a hydrate or solvate thereof is a temperature used in a conventional production process and is, for example, in a range of 0 to 60° C., and preferably 0 to 30° C. After precipitation, stirring is optionally performed for a predetermined time. It is acceptable time in manufacturing, for example, 1 hour or more.

Regarding 4'-epi-daunorubicin benzenesulfonate or a hydrate or solvate thereof, 4'-epi-daunorubicin is dissolved in a solvent C, and then benzenesulfonic acid monohydrate dissolved in a solvent D is added to this solution to thereby precipitate 4'-epi-daunorubicin benzenesulfonate or a hydrate or solvate thereof. Thereafter, the precipitate is collected by filtration and then optionally dried under reduced pressure.

As the solvent C, organic solvents used generally by a person skilled in the art can be used. The organic solvent usable as the solvent C is preferably halogenated solvents, specifically dichloromethane, chloroform, or the like, and more preferably dichloromethane. The amount of the solvent C used is not particularly limited as long as it enables dissolution of 4'-epi-daunorubicin, and is preferably in a range of 10 to 400 times the volume of 4'-epi-daunorubicin.

As the solvent D, organic solvents used generally by a person skilled in the art can be used. Examples of the organic solvent usable as the solvent D include methanol, ethanol, 1-propanol, 2-propanol, 1-butanol, 2-butanol, tert-butyl alcohol, acetone, ethyl acetate, tetrahydrofuran, 1,4-dioxane, toluene, acetonitrile, and the like, and methanol is preferable. The amount of the solvent D used is, for example, in a range of 0.02 to 0.2 times, and preferably 0.05 to 0.1 times, the volume of the solvent C. The amount of benzenesulfonic acid monohydrate used is, for example, in a range of 1 to 5 equivalents, and preferably 1 to 2 equivalents. The precipitation temperature is a temperature used in a conventional production process and is, for example, in a range of 0 to 30° C., and preferably 15 to 25° C. After precipitation, stirring is optionally performed for a predetermined time. It is acceptable time in manufacturing, for example, 1 hour or more.

It is also possible to prepare 4'-epi-daunorubicin benzenesulfonate or a hydrate or solvate thereof by another production method, for example, a method in which 4'-epi-daunorubicin is added to an aqueous solution of benzenesulfonic acid monohydrate to thereby dissolve 4'-epi-daunorubicin, and then an optional solvent is added to this solution to thereby precipitate 4'-epi-daunorubicin benzenesulfonate or a hydrate or solvate thereof.

In this case, organic solvents used generally by a person skilled in the art can be used as the optional solvent. Examples of the organic solvent usable as the optional solvent include methanol, ethanol, 1-propanol, 2-propanol, tert-butyl alcohol, acetone, tetrahydrofuran, 1,4-dioxane, acetonitrile, and the like, and ethanol and acetone are preferable. The amount of water used is, for example, in a range of 2.5 to 15 times, and preferably 5 to 10 times, the volume of 4'-epi-daunorubicin. The dissolution temperature of 4'-epi-daunorubicin is a temperature used in a conventional production process and is, for example, in a range of 20 to 60° C. The amount of the optional solvent used is, for example, in a range of 1 to 10 times, and preferably 1 to 5 times, the volume of water. The amount of benzene sulfonate monohydrate used is, for example, in a range of 1 to 5 equivalents, and preferably 1 to 2 equivalents.

Regarding 4'-epi-daunorubicin p-toluenesulfonate or a hydrate or solvate thereof, 4'-epi-daunorubicin is dissolved in a solvent E, and then p-toluenesulfonic acid monohydrate dissolved in a solvent F is added to this solution to thereby precipitate 4'-epi-daunorubicin p-toluenesulfonate or a hydrate or solvate thereof. Thereafter, the precipitate is collected by filtration and then optionally dried under reduced pressure.

As the solvent E, organic solvents used generally by a person skilled in the art can be used. The organic solvent usable as the solvent E is preferably a halogenated solvent, an amide-based solvent, or a sulfoxide-based solvent, specifically dichloromethane, chloroform, N,N-dimethylformamide, N,N-dimethylacetamide, dimethyl sulfoxide, or the like, and more preferably dichloromethane. The amount of the solvent E used is not particularly limited as long as it enables dissolution of 4'-epi-daunorubicin, and is preferably in a range of 10 to 400 times the volume of 4'-epi-daunorubicin.

As the solvent F, organic solvents used generally by a person skilled in the art can be used. Examples of the organic solvent usable as the solvent F include methanol, ethanol, 1-propanol, 2-propanol, 1-butanol, 2-butanol, tert-butyl alcohol, acetone, ethyl acetate, tetrahydrofuran, 1,4-dioxane, toluene, acetonitrile, and the like, and methanol is preferable. The amount of the solvent F used is, for example, in a range of 0.02 to 10 times, and preferably 0.05 to 5 times, the volume of the solvent E. The amount of p-toluenesulfonic acid monohydrate used is preferably in a range of 1 to 2 equivalents, and more preferably 1 to 1.5 equivalents. The precipitation temperature is a temperature used in a conventional production process and is, for example, in a range of 0 to 30° C., and preferably 15 to 25° C. After precipitation, stirring is optionally performed for a predetermined time. It is acceptable time in manufacturing, for example, 1 hour or more.

It is possible to further crystallize the precipitate of the organic acid salt of 4'-epi-daunorubicin or the hydrate or solvate thereof, produced as mentioned above.

Specifically, 4'-epi-daunorubicin oxalate or a hydrate or solvate thereof is suspended in water, and then dissolved at a temperature used in a conventional production process, for example, 20 to 60° C. Subsequently, this solution is cooled gradually, after addition of an optional solvent is completed. Although the temperature is optional, it is preferred to gradually cool the solution to 0 to 30° C. Thereafter, the crystal is collected by filtration and then optionally dried under reduced pressure.

As the optional solvent, organic solvents used generally by a person skilled in the art can be used. Examples of the organic solvent usable as the optional solvent include methanol, ethanol, 1-propanol, 2-propanol, tert-butyl alcohol, acetone, tetrahydrofuran, 1,4-dioxane, acetonitrile, and the like, and methanol and 2-propanol are preferable. The amount of water used is, for example, in a range of 5 to 20 times, and preferably 10 to 15 times, the volume of 4'-epi-daunorubicin. The amount of the optional solvent used is, for example, in a range of 1 to 10 times, and preferably 1 to 5 times, the volume of water.

4'-Epi-daunorubicin benzenesulfonate or a hydrate or solvate thereof is suspended in a solvent G, and then dissolved at a temperature used in a conventional production process, for example, 20 to 60° C. Subsequently, this solution is cooled gradually, after addition of a solvent H is completed. Although the temperature is optional, it is preferred to gradually cool the solution to 0 to 30° C. Thereafter, the crystal is collected by filtration and then optionally dried under reduced pressure.

The solvent G is, for example, water, N,N-dimethylformamide, N,N-dimethylacetamide, dimethyl sulfoxide, or the like, and preferably water. As the solvent H, organic solvents used generally by a person skilled in the art can be used. Examples of the organic solvent usable as the solvent H include methanol, ethanol, 1-propanol, 2-propanol, tert-butyl alcohol, acetone, tetrahydrofuran, 1,4-dioxane, acetonitrile, and the like, and ethanol and acetone are preferable. The amount of the solvent G used is, for example, in a range of 2.5 to 15 times, and preferably 5 to 10 times, the volume of 4'-epi-daunorubicin. The amount of the solvent H used is, for example, in a range of 1 to 10 times, and preferably 1 to 5 times, the volume of the solvent G.

4'-Epi-daunorubicin p-toluenesulfonate or a hydrate or solvate thereof is suspended in a mixed solution of an organic solvent and water, and then dissolved at a temperature used in a conventional production process, for example, 20 to 60° C. Subsequently, this solution is gradually cooled. Although the temperature is optional, it is preferred to gradually cool the solution to 0 to 30° C. Thereafter, the crystal is collected by filtration and then optionally dried under reduced pressure.

As the organic solvent, organic solvents used generally by a person skilled in the art can be used. Examples of the organic solvent include methanol, ethanol, 1-propanol, 2-propanol, tert-butyl alcohol, acetone, tetrahydrofuran, 1,4-dioxane, acetonitrile, and the like, and acetone is preferable. A ratio of the organic solvent to water is, for example, in a range of 1:1 to 5:1, and preferably 1:1 to 2:1. The amount of the mixed solution used is, for example, in a range of 10 to 30 times, and preferably 10 to 20 times, the volume of 4'-epi-daunorubicin.

It is also possible to crystallize 4'-epi-daunorubicin p-toluenesulfonate or a hydrate or solvate thereof in the following manner.

4'-Epi-daunorubicin p-toluenesulfonate or a hydrate or solvate thereof is suspended in a solvent I, and then dissolved at a temperature used in a conventional production process, for example, 20 to 60° C. A solvent J is added to this solution to thereby crystallize, followed by gradual cooling, optionally. Thereafter, the crystal is collected by filtration and then optionally dried under reduced pressure.

The solvent I is, for example, N,N-dimethylformamide, N,N-dimethylacetamide, dimethyl sulfoxide, or the like, and preferably N,N-dimethylformamide. As the solvent J, water or organic solvents used generally by a person skilled in the art can be used. Examples of the organic solvent usable as the solvent J include methanol, ethanol, 1-propanol, 2-propanol, tert-butyl alcohol, acetone, ethyl acetate, toluene, and the like, and ethanol is preferable. The amount of the solvent I used is, for example, in a range of 2.5 to 15 times, and preferably 5 to 10 times, the volume of 4'-epi-daunorubicin. The amount of the solvent J used is, for example, in a range of 1 to 5 times, and preferably 2 to 2.5 times, the volume of the solvent I.

In the process of producing an organic acid salt of 4'-epi-daunorubicin or a hydrate or solvate thereof from 4'-epi-daunorubicin, a removal ratio of 13-dihydroepi-daunorubicin and that of 4'-epi-feudomycin by performing a single precipitation are respectively 25% or more and 37% or more based on the amount contained in 4'-epi-daunorubicin represented by the formula (1) which is a starting material. A removal ratio of 13-dihydroepi-daunorubicin and that of 4'-epi-feudomycin by performing a single crystallization of an organic acid salt of 4'-epi-daunorubicin or a hydrate or solvate thereof obtained as the precipitate are respectively 77% or more and 63% or more based on the amount contained in the organic acid salt of 4'-epi-daunorubicin or a hydrate or solvate thereof obtained as the precipitate.

The amount of impurities contained in the precipitate of the organic acid salt of 4'-epi-daunorubicin represented by the formula (2) or a hydrate or solvate thereof produced by the present invention (percentage of a peak area of impurities based on the sum of peak areas excluding a peak of an organic acid in an HPLC analysis) is not fixed since it varies depending on the amount of impurities contained in 4'-epi-daunorubicin used as a starting material. As a result of a single precipitation, the amount of 13-dihydroepi-daunorubicin can become 2.6% or less, and the amount of 4'-epifeudomycin can become 3.5% or less. As a result of further carrying out a single crystallization, the amount of 13-dihydroepi-daunorubicin in a crystal of an organic acid salt of 4'-epi-daunorubicin or a hydrate or solvate thereof can become 1.6% or less, and the amount of 4'-epi-feudomycin can become 0.9% or less. Use of a high-purity starting material enables further decrease in the amount of these impurities.

HPLC purity of the precipitate of the organic acid salt of 4'-epi-daunorubicin represented by the formula (2) or a hydrate or solvate thereof produced by the present invention is 90% or more. It is possible to improve HPLC purity to 95% or more by further crystallizing the organic acid salt of 4'-epi-daunorubicin or a hydrate or solvate thereof obtained as the precipitate.

Using the organic acid salt of 4'-epi-daunorubicin represented by the formula (2) or a hydrate or solvate thereof, produced by the present invention, high-purity epirubicin or a salt thereof (for example, a pharmaceutically acceptable salt) can be produced, for example, by the method disclosed in Patent Document 2. To produce epirubicin hydrochloride, first, an organic acid salt of 4'-epi-daunorubicin or a hydrate or solvate thereof is reacted with a brominating agent in the presence of a ketal agent to obtain a bromoketal body. Next, the bromoketal body is treated with ketone-based solvents under acidic conditions to obtain a bromoketone body. Furthermore, the bromoketone body is hydrolyzed in the presence of a carboxylic acid metal salt to give a solution containing epirubicin as a main component. The solution containing epirubicin as a main component is passed through an ion exchange resin (chloride ion type) to give an aqueous solution of epirubicin hydrochloride, which is then purified by an adsorbing resin. A main fraction of the epirubicin hydrochloride solution is concentrated to obtain epirubicin hydrochloride.

More specifically, an organic solvent is added to an organic acid salt of 4'-epi-daunorubicin or a hydrate or solvate thereof. There is no particular limitation on type of organic solvent as long as the reaction proceeds, and these solvents may be used alone, or several types of solvents may be mixed. A mixing ratio of solvents may be an optional ratio. Alcohols, ethers, and an optional mixed solvent composed of them are preferable. A mixed solvent of methanol and 1,4-dioxane is more preferable. Next, the organic acid salt of 4'-epi-daunorubicin or a hydrate or solvate thereof is reacted with a ketal agent and a brominating agent to give a bromoketal body. The ketal agent used is, for example, an alkyl orthoformate. It is possible to use, as the alkyl orthoformate, for example, trimethyl orthoformate, triethyl orthoformate, tripropyl orthoformate, tributyl orthoformate, and the like. The ketal agent is preferably trimethyl orthoformate. A brominating agent is suitably bromine. After completion of the reaction, an acid scavenger, for example, propylene oxide is added to the solution in order to remove excess acid existing in the reaction solution. After addition of the acid scavenger, the solution is concentrated and a poor solvent is added to the concentrated solution to thereby isolate the bromoketal body as the precipitate. It is possible to use, as the poor solvent, ethers. The poor solvent is preferably diisopropyl ether.

The precipitate of the bromoketal body can be used for the subsequent step without drying. The wet or dry bromoketal body is reacted by dissolving in an aqueous solution of hydrobromic acid and ketone-based solvents. It is possible to use, as ketone-based solvents, acetone, methyl ethyl ketone, and the like. The ketone-based solvent is preferably acetone. After the reaction, the bromoketone body can be converted into epirubicin without isolation. Namely, the solution of the bromoketone body is mixed with a carboxylic acid alkali metal salt and then the pH is adjusted with a base to obtain a solution containing epirubicin as a main component. It is possible to use, as the carboxylic acid alkali metal salt, sodium formate, sodium acetate, potassium formate, potassium acetate, and the like. The carboxylic acid alkali metal salt is preferably sodium formate. It is possible to use, as the base, an alkali metal hydroxide. The base is preferably sodium hydroxide. The pH is preferably adjusted in a range of 4.0 to 6.0, and more preferably 4.5 to 5.5.

To isolate epirubicin as a hydrochloride from the solution containing epirubicin as a main component, the solution is diluted with water and then the pH is adjusted by adding hydrochloric acid. The pH is preferably adjusted in a range of 2.0 to 4.0, and more preferably 2.5 to 3.5. Next, the solution thus adjusted is passed through an ion exchange resin (chloride ion type) to obtain an aqueous solution of epirubicin hydrochloride. Furthermore, this aqueous solution is adsorbed to the adsorbing resin and then purified by passing water, and a mixed solution of an organic solvent and water in this order through the adsorbing resin. It is possible to use, as the organic solvent, methanol, ethanol, 1-propanol, 2-propanol, acetone, and the like. The organic solvent is preferably methanol. The main fraction of epirubicin hydrochloride is concentrated and further concentrated by adding ethanol to this concentrated solution, followed by concentration and drying to obtain epirubicin hydrochloride.

As described above, the present invention provides a novel production intermediate, wherein 13-dihydroepi-daunorubicin and 4'-epi-feudomycin, which are typical impurities possibly contained in 4'-epi-daunorubicin, have been sufficiently removed, a method of efficiently producing this intermediate using 4'-epi-daunorubicin as a starting material, and a method of efficiently producing high-purity epirubicin or a salt thereof (for example, a pharmaceutically acceptable salt) using this intermediate.

EXAMPLES

Examples and Comparative Examples of the present invention will be illustrated below, but the present invention is not limited to the following Examples.

HPLC purity of each of 4'-epi-daunorubicin, 4'-epi-daunorubicin oxalate, 4'-epi-daunorubicin benzenesulfonate, 4'-epi-daunorubicin p-toluenesulfonate, and 4'-epi-daunorubicin hydrochloride is a peak area ratio of 4'-epi-daunorubicin when HPLC analysis is performed under the following conditions. A removal ratio of 13-dihydroepi-daunorubicin and 4'-epi-feudomycin was calculated in the following manner. That is, when HPLC analysis of 4'-epi-daunorubicin or a 4'-epi-daunorubicin salt is performed under the following conditions, values obtained by dividing a peak area of 13-dihydroepi-daunorubicin and that of 4'-epi-feudomycin by a peak area of 4'-epi-daunorubicin were regarded as the content of 13-dihydroepi-daunorubicin and that of 4'-epi-feudomycin, respectively.

HPLC Conditions
Column: Kinetex 2.6u C18 100 A, 2.6 μm, 3.0×150 mm (manufactured by Phenomenex Inc.)
Mobile phase A: 5 mmol/L sodium lauryl sulfate+10 mmol/L sodium phosphate buffer (pH 2.2)
Mobile phase B: acetonitrile
Flow rate: 0.5 nil/min.
Temperature: 40° C.
Measurement wavelength: 254 nm
Analysis time: 13 minutes Data collection time: 2.0 to 13.0 minutes
Gradient Conditions:

| Time (min) | % of mobile phase A | % of mobile phase B |
|---|---|---|
| 0 | 75.0% | 25.0% |
| 10.00 | 35.0% | 65.0% |
| 10.01 | 75.0% | 25.0% |
| 13.00 | 75.0% | 25.0% |

Under the above-mentioned measurement conditions, peaks of 4'-epi-daunorubicin, 13-dihydroepi-daunorubicin, and 4'-epi-feudomycin are confirmed at about 8.7, about 8.1, and about 8.5 minutes, respectively.

HPLC purity of epirubicin hydrochloride is a peak area ratio of epirubicin when HPLC analysis is performed under the following conditions.
HPLC Conditions
Column: Senshu Pak ODS-1301S 4.6×300 mm (manufactured by Senshu Scientific Co., Ltd.)
Mobile phase: (0.3 (w/v) % sodium lauryl sulfate+0.14 (v/v) % phosphate buffer)/acetonitrile solution=1/1
Flow rate: 1.1 ml/min.
Temperature: 25° C.
Measurement wavelength: 254 nm
Analysis time: 30 minutes Under the above-mentioned measurement conditions, a peak of epirubicin is confirmed at about 11 minutes.

Example 1

150 mg of 4'-epi-daunorubicin (HPLC purity of 79.9%) was dissolved in 60 mL of dichloromethane. To this solution was added a solution of 299 mg of oxalic acid in 15 mL of methanol, and the mixture was stirred for 22 hours at 15 to 25° C. The precipitate was collected by filtration and then dried under reduced pressure to obtain 150 mg of 4'-epi-daunorubicin oxalate (129 mg as 4'-epi-daunorubicin). Yield was 85.5% and HPLC purity was 94.8%. A removal ratio of 13-dihydroepi-daunorubicin and that of 4'-epi-feudomycin were respectively 52% and 51%. As a result of HPLC analysis, the oxalic acid peak in 4'-epi-daunorubicin oxalate completely agreed with the retention time of oxalic acid (special grade chemical).

$^1$H-NMR (400 MHz, D2O) δ (ppm); 7.55 (1H, dd), 7.35 (1H, d), 7.27 (1H, d), 5.30 (1H, d), 4.68 (1H, m), 3.86 (1H, m), 3.78 (3H, s), 3.26 (2H, m), 2.76 (1H, d), 2.56 (1H, d), 2.31 (3H, d), 2.14 (2H, m), 1.98 (1H, dd), 1.81 (1H, ddd), 1.22 (3H, d)

MS (ESI, positive); m/z 528[M+H]+

Example 2

5.0 g of 4'-epi-daunorubicin (HPLC purity of 76.8%) was dissolved in 2,000 mL of dichloromethane. To this solution was added a solution of 10 g of oxalic acid in 400 mL of methanol, and the mixture was stirred for 22 hours at 15 to 25° C. The precipitate was collected by filtration and then dried under reduced pressure to obtain 5.1 g of 4'-epi-daunorubicin oxalate (4.4 g as 4'-epi-daunorubicin). Yield was 88.3% and HPLC purity was 94.4%. A removal ratio of 13-dihydroepi-daunorubicin and that of 4'-epi-feudomycin were respectively 48% and 48%.

Example 3

150 mg of 4'-epi-daunorubicin (HPLC purity of 79.9%) was dissolved in 60 mL of dichloromethane. To this solution was added a solution of 419 mg of oxalic acid dihydrate in 12 mL of methanol, and the mixture was stirred for 20 hours at 15 to 25° C. The precipitate was collected by filtration and then dried under reduced pressure to obtain 153 mg of 4'-epi-daunorubicin oxalate (132 mg as 4'-epi-daunorubicin). Yield was 88.1% and HPLC purity was 95.3%. A removal ratio of 13-dihydroepi-daunorubicin and that of 4'-epi-feudomycin were respectively 56% and 58%.

Example 4

150 mg of 4'-epi-daunorubicin (HPLC purity of 79.9%) was dissolved in a solution of 51 mg of oxalic acid in 1.5 mL of water. To this solution was added 1.5 mL of methanol, and the mixture was stirred for 22 hours at 15 to 25° C. The precipitate was collected by filtration and then dried under reduced pressure to obtain 135 mg of 4'-epi-daunorubicin oxalate (109 mg as 4'-epi-daunorubicin). Yield was 72.8% and HPLC purity was 95.9%. A removal ratio of 13-dihydroepi-daunorubicin and that of 4'-epi-feudomycin were respectively 76% and 61%.

Example 5

1.0 g of 4'-epi-daunorubicin (HPLC purity of 75.8%) was dissolved in 100 mL of dichloromethane. To this solution was added a solution of a solution of 334 mg of benzenesulfonic acid monohydrate in 5 mL of methanol, and the mixture was stirred for 19 hours at 15 to 25° C. The precipitate was collected by filtration and then dried under reduced pressure to obtain 1.12 g of 4'-epi-daunorubicin benzenesulfonate (0.88 g as 4'-epi-daunorubicin). Yield was 87.7% and HPLC purity was 91.6%. A removal ratio of 13-dihydroepi-daunorubicin and that of 4'-epi-feudomycin were respectively 25% and 37%.

$^1$H-NMR (400 MHz, D2O) δ (ppm); 7.74 (2H, m, C$_6$H$_5$SO$_3$H), 7.64 (1H, dd), 7.50 (3H, m, C$_6$H$_5$SO$_3$H), 7.43 (1H, d), 7.36 (1H, d), 5.39 (1H, d), 4.76 (1H, m), 3.99 (1H, m), 3.88 (3H, s), 3.36 (2H, m), 2.86 (1H, d), 2.65 (1H, d), 2.40 (3H, s), 2.22 (2H, m), 2.06 (1H, dd), 1.90 (1H, ddd), 1.31 (3H, d)

MS (ESI, positive); m/z 528[M+H]+

Example 6

1.0 g of 4'-epi-daunorubicin (HPLC purity of 75.8%) was dissolved in 100 mL of dichloromethane. To this solution was added a solution of 361 mg of p-toluenesulfonic acid monohydrate in 5 mL of methanol, and the mixture was stirred for 22 hours at 15 to 25° C. The precipitate was collected by filtration and then dried under reduced pressure to obtain 1.08 g of 4'-epi-daunorubicin p-toluenesulfonate (0.84 g as 4'-epi-daunorubicin). Yield was 83.8% and HPLC purity was 92.8%. A removal ratio of 13-dihydroepi-daunorubicin and that of 4'-epi-feudomycin were respectively 37% and 47%.

$^1$H-NMR (400 MHz, D2O) δ (ppm); 7.59 (1H, d, p-MeC$_6$H$_4$SO$_3$H), 7.58 (1H, dd), 7.34 (1H, d), 7.30 (1H, d), 7.26 (1H, d, p-MeC$_6$H$_4$SO$_3$H), 5.38 (1H, d), 4.74 (1H, m), 3.98 (1H, m), 3.83 (3H, s), 3.36 (2H, m), 2.82 (1H, d), 2.62 (1H, d), 2.40 (3H, s), 2.30 (3H, s, p-MeC$_6$H$_4$SO$_3$H), 2.23 (2H, m), 2.03 (1H, dd), 1.91 (1H, ddd), 1.32 (3H, d)

MS (ESI, positive); m/z 528[M+H]+

Comparative Example 1

Using 150 mg of 4'-epi-daunorubicin (HPLC purity of 79.9%), 4'-epi-daunorubicin hydrochloride was obtained in accordance with the method for conversion into a hydrochloride salt of Example 2 of Patent Document 5. Yield was 77.0% and HPLC purity was 84.3%. A removal ratio of 13-dihydroepi-daunorubicin and that of 4'-epi-feudomycin were respectively 0% and 6%.

Comparative Example 2

Using 150 mg of 4'-epi-daunorubicin (HPLC purity of 79.9%), 4'-epi-daunorubicin hydrochloride was obtained in accordance with the method for conversion into a hydrochloride salt of Non-Patent Document 2. Yield was 80.8% and HPLC purity was 77.0%. A removal ratio of 13-dihydroepi-daunorubicin and that of 4'-epi-feudomycin were respectively 3% and 9%.

Comparative Example 3

Using 150 mg of 4'-epi-daunorubicin (HPLC purity of 79.9%), 4'-epi-daunorubicin hydrochloride was obtained in accordance with Example 9 of Patent Document 4. Yield was 92.1% and HPLC purity was 80.2%. A removal ratio of 13-dihydroepi-daunorubicin and that of 4'-epi-feudomycin were respectively 0% and 4%.

Removal ratios of 13-dihydroepi-daunorubicin and 4'-epi-feudomycin, HPLC purities, and yields are shown in Table 1 below.

TABLE 1

| | Removal ratio of 13-dihydroepi-daunorubicin | Removal ratio of 4'-epi-feudomycin | HPLC purity | Yield |
|---|---|---|---|---|
| Example 1 | 52% | 51% | 94.8% | 85.5% |
| Example 2 | 48% | 48% | 94.4% | 88.3% |
| Example 3 | 56% | 58% | 95.3% | 88.1% |
| Example 4 | 76% | 61% | 95.9% | 72.8% |
| Example 5 | 25% | 37% | 91.6% | 87.7% |
| Example 6 | 37% | 47% | 92.8% | 83.8% |
| Comparative Example 1 | 0% | 6% | 84.3% | 77.0% |
| Comparative Example 2 | 3% | 9% | 77.0% | 80.8% |
| Comparative Example 3 | 0% | 4% | 80.2% | 92.1% |

As a result of a comparison between a removal ratio of 13-dihydroepi-daunorubicin and 4'-epi-feudomycin of an organic acid salt of 4'-epi-daunorubicin represented by the formula (2) obtained in Examples 1 to 6, and that of 4'-epi-daunorubicin hydrochloride obtained in Comparative Examples 1 to 3, impurities were efficiently removed in the organic acid salt of 4'-epi-daunorubicin represented by the formula (2).

Example 7

2.65 g of 4'-epi-daunorubicin oxalate (2.00 g as 4'-epi-daunorubicin, HPLC purity of 92.9%) was suspended in 20 mL of water. The suspension was warmed to 60° C. and dissolved. To this solution was added 20 mL of methanol, and cooled to 25° C. gradually. The crystal was collected by filtration and then dried under reduced pressure to obtain 1.83 g of 4'-epi-daunorubicin oxalate (1.70 g as 4'-epi-daunorubicin). Yield was 85.1% and HPLC purity was 99.2%. A removal ratio of 13-dihydroepi-daunorubicin and that of 4'-epi-feudomycin were respectively 92% and 89%. Polarization was observed for 4'-epi-daunorubicin oxalate thus obtained.

Example 8

262 mg of 4'-epi-daunorubicin oxalate (200 mg as 4'-epi-daunorubicin, HPLC purity of 92.9%) was suspended in 2.0 mL of water. The suspension was warmed to 60° C. and dissolved. To this solution was added 2.0 mL of 2-propanol, and cooled to 25° C. gradually. The crystal was collected by filtration and then dried under reduced pressure to obtain 197 mg of 4'-epi-daunorubicin oxalate (178 mg as 4'-epi-daunorubicin). Yield was 89.1% and HPLC purity was 98.6%. A removal ratio of 13-dihydroepi-daunorubicin and that of 4'-epi-feudomycin were respectively 90% and 89%. Polarization was observed for 4'-epi-daunorubicin oxalate thus obtained.

Example 9

64 mg of 4'-epi-daunorubicin benzenesulfonate (50 mg as 4'-epi-daunorubicin, HPLC purity of 91.6%) was suspended in 250 μL of water. The suspension was warmed to 45° C. and dissolved. To this solution was added 250 μL of ethanol, and cooled to 25° C. gradually. The crystal was collected by filtration to obtain 31 mg of 4'-epi-daunorubicin benzenesulfonate (27 mg as 4'-epi-daunorubicin). Yield was 53.3% and HPLC purity was 98.7%. A removal ratio of 13-dihydroepi-daunorubicin and that of 4'-epi-feudomycin were respectively 91% and 80%. Polarization was observed for 4'-epi-daunorubicin benzenesulfonate thus obtained.

Example 10

64 mg of 4'-epi-daunorubicin benzenesulfonate (50 mg as 4'-epi-daunorubicin, HPLC purity of 91.6%) was suspended in 250 μL of water. The suspension was warmed to 45° C. and dissolved. To this solution was add 250 μL of acetone, and cooled to 25° C. gradually. The crystal was collected by filtration to obtain 41 mg of 4'-epi-daunorubicin benzenesulfonate (35 mg as 4'-epi-daunorubicin). Yield was 69.2% and HPLC purity was 98.1%. A removal ratio of 13-dihydroepi-daunorubicin and that of 4'-epi-feudomycin were respectively 83% and 77%. Polarization was observed for 4'-epi-daunorubicin benzenesulfonate thus obtained.

Example 11

61 mg of 4'-epi-daunorubicin p-toluenesulfonate (50 mg as 4'-epi-daunorubicin, HPLC purity of 92.8%) was suspended in a mixed solution of 250 μL of water and 375 μL of acetone. The suspension was warmed to 45° C. and dissolved. Subsequently, this solution was gradually cooled to a temperature in a range of 0 to 5° C. The crystal was collected by filtration and then dried under reduced pressure to obtain 31 mg of 4'-epi-daunorubicin p-toluenesulfonate (27 mg as 4'-epi-daunorubicin). Yield was 53.6% and HPLC purity was 98.4%. A removal ratio of 13-dihydroepi-daunorubicin and that of 4'-epi-feudomycin were respectively 83% and 63%. Polarization was observed for 4'-epi-daunorubicin p-toluenesulfonate thus obtained.

Example 12

658 mg of 4'-epi-daunorubicin p-toluenesulfonate (500 mg as 4'-epi-daunorubicin, HPLC purity of 91.0%) was added to 5 mL of N,N-dimethylformamide, and dissolved at 30° C. To this solution was added 12.5 mL of ethanol, and stirred. The crystal was collected by filtration and then dried under reduced pressure to obtain 447 mg of 4'-epi-daunorubicin p-toluenesulfonate (365 mg as 4'-epi-daunorubicin). Yield was 73.0% and HPLC purity was 97.4%. A removal ratio of 13-dihydroepi-daunorubicin and that of 4'-epi-feudomycin were respectively 77% and 68%. Polarization was observed for 4'-epi-daunorubicin p-toluenesulfonate thus obtained.

Comparative Example 4

Using 8.7 g (HPLC purity of 84.3%) of 4'-epi-daunorubicin hydrochloride obtained by the method of Comparative Example 3, a crystalline 4'-epi-daunorubicin hydrochloride was obtained in accordance with Example 2 of Patent Document 6. Yield was 76.6% and HPLC purity was 94.0%. A removal ratio of 13-dihydroepi-daunorubicin and that of 4'-epi-feudomycin were respectively 75% and 55%.

Removal ratios of 13-dihydroepi-daunorubicin and 4'-epi-feudomycin, HPLC purities, and yields are shown in Table 2 below.

TABLE 2

| | Removal ratio of 13-dihydroepi-daunorubicin | Removal ratio of 4'-epi-feudomycin | HPLC purity | Yield |
|---|---|---|---|---|
| Example 7 | 92% | 89% | 99.2% | 85.1% |
| Example 8 | 90% | 89% | 98.6% | 89.1% |
| Example 9 | 91% | 80% | 98.7% | 53.3% |
| Example 10 | 83% | 77% | 98.1% | 69.2% |
| Example 11 | 83% | 63% | 98.4% | 53.6% |
| Example 12 | 77% | 68% | 97.4% | 73.0% |
| Comparative Example 4 | 75% | 55% | 94.0% | 76.6% |

A comparison was made between each removal ratio of 13-dihydroepi-daunorubicin and 4'-epi-feudomycin of an organic acid salt of 4'-epi-daunorubicin represented by the formula (2) obtained in Examples 7 to 12 and that of a crystalline 4'-epi-daunorubicin hydrochloride obtained in Comparative Example 4. As a result, crystallization of 4'-epi-daunorubicin hydrochloride also exhibited a purification effect on 13-dihydroepi-daunorubicin and 4'-epi-feudomycin. However, it has been found that the effect is not sufficient as compared with an organic acid salt of 4'-epi-daunorubicin and there is a need to repeat crystallization so as to obtain high-purity 4'-epi-daunorubicin hydrochloride. Repetition of crystallization is unsuitable from the viewpoints (yield, operability, and production cost) of an industrial production method.

Example 13

4'-Epi-daunorubicin oxalate (6.27 g as 4'-epi-daunorubicin, HPLC purity of 99.2%) produced by the method of Example 7, 67 mL of methanol, 67 mL of 1,4-dioxane and 12 mL of trimethyl orthoformate were combined, and then 1.1 mL of bromine was added to the mixture. After stirring for 4 hours at room temperature, 3.2 mL of propylene oxide was added to the mixture, and stirred for further 0.5 hour. The mixture was concentrated to 60 mL, and the concentrate was added to 740 mL of diisopropyl ether to form the precipitate of bromo ketal. The resulting precipitate was filtered, and this wet cake was added to the mixture of 142 mL of water and 146 mL of acetone. To this mixture was added 4.2 mL of hydrobromic acid, and the mixture was stirred for 21 hours at room temperature. Subsequently, a previously prepared mixture of 10 g of sodium formate and 42 mL of water was added to this reaction mixture. After stirring for 24 hours at room temperature, pH was adjusted to 5 with an aqueous sodium hydroxide, followed by stirring for 24 hours. This solution was adjusted to pH 3 with hydrochloric acid, and then concentrated. The resulting concentrate was diluted with water to adjust its volume to 2,000 mL. The solution was passed through an ion exchange resin (chloride ion type), and then epirubicin hydrochloride containing solution was obtained by passing water through the ion exchange resin. Furthermore, this solution was absorbed on an adsorbing resin, and epirubicin hydrochloride solution was eluted with water, water/methanol (=80/20 (v/v)), and water/methanol (=70/30 (v/v)) in this order. A main fraction was concentrated and ethanol was added to the concentrate, followed by further concentration. The resulting residue was dried under vacuum to give 3.29 g of epirubicin hydrochloride (2.99 g as epirubicin). Yield was 46.6% and HPLC purity was 99.2%.

Example 14

Using 4'-epi-daunorubicin benzenesulfonate of the formula (2) (6.27 g as 4'-epi-daunorubicin, HPLC purity of 98.7%) produced by the method of Example 9, 2.48 g of epirubicin hydrochloride (2.22 g as epirubicin) was obtained in the same manner as in Example 13. Yield was 34.3% and HPLC purity was 97.9%.

Example 15

Using 4'-epi-daunorubicin p-toluenesulfonate of the formula (2) (6.27 g as 4'-epi-daunorubicin, HPLC purity of 98.7%) produced by the method of Example 11, 2.50 g of epirubicin hydrochloride (2.26 g as epirubicin) was obtained in the same manner as in Example 13. Yield was 35.0% and HPLC purity was 98.1%.

Comparative Example 5

Using 4'-epi-daunorubicin hydrochloride (6.27 g as 4'-epi-daunorubicin, HPLC purity of 93.1%) produced by the method of Comparative Example 4, 4.02 g of epirubicin hydrochloride (3.41 g as epirubicin) was obtained in the same manner as in Example 13. Yield was 52.8% and HPLC purity was 93.7%.

A comparison was made between HPLC purity of epirubicin hydrochlorides obtained in Examples 13 to 15 and HPLC purity of epirubicin hydrochloride obtained in Comparative Example 5. As a result, HPLC purity of epirubicin hydrochloride produced by using an organic acid salt of 4'-epi-daunorubicin of the formula (2) was higher than that of epirubicin hydrochloride produced by using 4'-epi-daunorubicin hydrochloride.

INDUSTRIAL APPLICABILITY

According to the method of the present invention, it is possible to produce high-purity epirubicin or a salt thereof by using a high-purity organic acid salt of 4'-epi-daunorubicin represented by the formula (2), or a hydrate or solvate thereof as a novel production intermediate. According to the method of the present invention, unlike a method in which 4'-epi-daunorubicin hydrochloride is used, 13-dihydroepi-daunorubicin and 4'-epi-feudomycin, which are typical impurities possibly contained in 4'-epi-daunorubicin can be effectively removed by performing a single precipitation in the process for producing an organic acid salt of 4'-epi-daunorubicin or a hydrate or solvate thereof. It is also possible to further remove these impurities by performing a single crystallization of the precipitate of the thus obtained organic acid salt of 4'-epi-daunorubicin or the hydrate or solvate thereof.

Therefore, it is possible to obtain a compound of the formula (2) which is used for effectively producing high-purity epirubicin or a salt thereof while keeping a small number of times of purification (short production process) as compared with conventional 4'-epi-daunorubicin hydrochloride, and thus the method of the present invention is significantly useful in the field of industrial production of epirubicin.

The invention claimed is:

1. A method of producing an organic acid salt of 4'-epi-daunorubicin or a hydrate or solvate thereof, comprising a step of mixing 4'-epi-daunorubicin of the following formula (1):

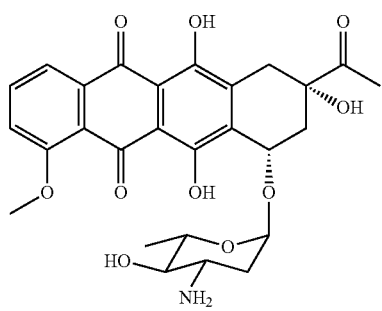

(1)

with an organic acid in a solvent to form an organic acid salt of 4'-epi-daunorubicin of the following formula (2):

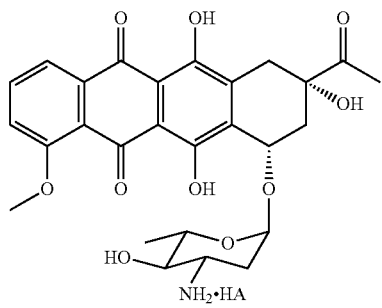

(2)

wherein HA represents an organic acid,
or a hydrate or solvate thereof,
wherein the organic acid salt of the 4'-epi-daunorubicin is selected from the group consisting of an oxalate, a benzenesulfonate and a p-toluenesulfonate.

2. The method according to claim 1, wherein the step of forming the organic acid salt of the 4'-epi-daunorubicin or hydrate or solvate thereof comprises forming a precipitate of the organic acid salt of the 4'-epi-daunorubicin or hydrate or solvate thereof.

3. The method according to claim 1, wherein the step of forming the organic acid salt of the 4'-epi-daunorubicin or hydrate or solvate thereof comprises crystallizing the organic acid salt of the 4'-epi-daunorubicin or hydrate or solvate thereof.

4. A method of producing epirubicin or a salt thereof, comprising a step of producing epirubicin of the following formula (3):

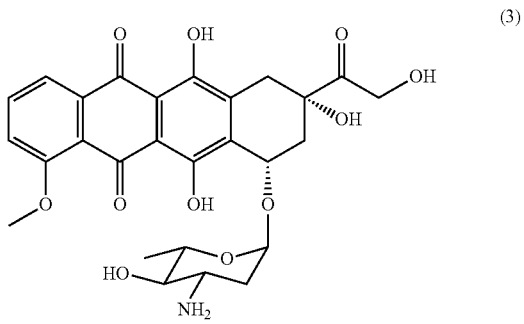 [SMILES: COc1cccc2c1C(=O)c1c(O)c3c(c(O)c1C2=O)C[C@@](O)(C(=O)CO)C[C@@H]3OC1CC(N)C(O)C(C)O1]

(3)

or a salt thereof using, as an intermediate, an organic acid salt of 4'-epi-daunorubicin or a hydrate or solvate thereof, produced by the method according to claim 1.

5. The method according to claim 4, wherein a final product is epirubicin hydrochloride.

6. An organic acid salt of 4'-epi-daunorubicin of the following formula (4):

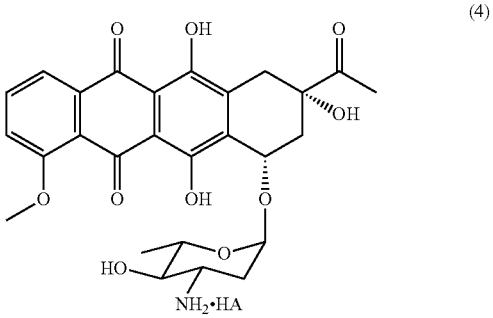

(4)

wherein HA represents oxalic acid, benzenesulfonic acid, or p-toluenesulfonic acid, or a hydrate or solvate thereof.

7. An organic acid salt of 4'-epi-daunorubicin or a hydrate or solvate thereof, having a HPLC purity of 90% or more, wherein the organic acid salt of the 4'-epi-daunorubicin is selected from the group consisting of an oxalate, a benzenesulfonate and a p-toluenesulfonate.

8. The method according to claim 1, wherein the 4'-epi-daunorubicin is mixed with the organic acid in the presence of an impurity selected from the group consisting of 13-dihydroepi-daunorubicin and 4'-epi-feudomycin.

9. The method according to claim 1, wherein the organic acid salt of the 4'-epi-daunorubicin or a hydrate or solvate thereof has a HPLC purity of 90% or more.

* * * * *